(12) United States Patent
Wille (10) Patent No.: US 7,399,493 B2
(45) Date of Patent: Jul. 15, 2008

(54) ANTI-IRRITANT BOTANICALS

(76) Inventor: John J. Wille, 9 Georgetown Chesterfield Rd., Trenton, NJ (US) 08620

( * ) Notice: Subject to any disclaimer, the term of this patent is extended or adjusted under 35 U.S.C. 154(b) by 53 days.

(21) Appl. No.: 11/183,495

(22) Filed: Jul. 18, 2005

(65) Prior Publication Data

US 2006/0062861 A1    Mar. 23, 2006

Related U.S. Application Data

(60) Provisional application No. 60/588,460, filed on Jul. 16, 2004.

(51) Int. Cl.
*A61K 36/899* (2006.01)
(52) U.S. Cl. .................................... 424/750
(58) Field of Classification Search ........................ None
See application file for complete search history.

(56) References Cited

U.S. PATENT DOCUMENTS

| | | | |
|---|---|---|---|
| 4,908,213 A | 3/1990 | Govil et al. | |
| 4,950,481 A * | 8/1990 | Keri et al. | .................. 424/750 |
| 5,252,604 A | 10/1993 | Nagy et al. | |
| 5,393,526 A | 2/1995 | Castro | |
| 5,516,793 A | 5/1996 | Duffy | |
| 5,545,407 A | 8/1996 | Hall et al. | |
| 5,618,577 A | 4/1997 | Pearson et al. | |
| 5,686,100 A | 11/1997 | Wille et al. | |
| 5,716,987 A | 2/1998 | Wille | |
| 5,843,979 A | 12/1998 | Wille et al. | |
| 5,912,010 A | 6/1999 | Wille et al. | |
| 6,423,747 B1 | 7/2002 | Lanzendoerfer et al. | |
| 6,670,395 B1 | 12/2003 | Wille | |
| 2001/0022978 A1 | 9/2001 | Lacharriere et al. | |

FOREIGN PATENT DOCUMENTS

| | | |
|---|---|---|
| EP | 0 314 528 A1 | 10/1988 |
| EP | 0 354 554 A2 | 8/1989 |
| JP | 2002114701 A * | 4/2002 |
| WO | WO 91/14441 | 10/1991 |
| WO | WO 97/18782 | 5/1997 |

OTHER PUBLICATIONS benoverby.wordpress.com, www.jupiterimages.com, www.bigthings.ca, www.old-picture.com.*
Rediscovering Natural Products, A. Maureen Rouhi, C&EN, Oct. 13, 2003.
Novel Plant-Derived Anti-Irritants, John J. Wille, Ph.D., Journal of Cosmetic Science, 54(1), 2003, pp. 106-107.
Plant-Derived Anti-Irritants, John J. Wille, Ph.D., Cosmetics & Toiletries Magazine, vol. 118, No. 8, Aug. 2003.
Thixogel Novel Topical Delivery Systems for Hydrophobic Plant Actives, John J. Wille, Ph.D., Delivery System Handbook for Personal Care and Cosmetic Products, 2005, p. 761-794.

* cited by examiner

*Primary Examiner*—Christopher R. Tate
*Assistant Examiner*—Deborah A. Davis
(74) *Attorney, Agent, or Firm*—Milde & Hoffberg, LLP (57) ABSTRACT

Anti-irritant botanical extracts, and a method for screening, and then preparing, anti-irritant botanical extracts for use in topical formulations, providing a natural ingredient capable of preventing skin irritation when in combination with other active and inactive ingredients that have the potential to irritant skin.

3 Claims, 10 Drawing Sheets

Antioxidant activity of standard antioxidants (50 µg/ml): Vitamin E(□), Ascorbic acid, Ascorbyl palmitate, and Quercetin dihydrate (X).

Figure 1.

Antioxidant activity of some tested botanicals: CTS (X), AOB (◊), GTL (□), GOL/RSC(○).

Figure 2.

Table 1. Relative Antioxidant Activity of Some Novel Botanicals

| Botanical Extract | Relative Extract Antioxidant Activity (Extract Concentration at the EC 50 point) |
|---|---|
| Autumn Olive Berry | 0.018 |
| Corn Tassel Spikelet | 0.022 |
| Green Tea Leaves | 0.05 |
| Green Onion Leaves | 1.3 |
| Red Swiss Chard | 1.3 |

Figure 2A

Table 2.
HPLC Chromatographic Data
*Corn Tassel Methanol Extract: UV detector set at 225nm.*

| Peaks | Elution times (min) | Area (%) |
|---|---|---|
| 1. | 7.52 | 26 |
| 2. | 8.25 | 43 |
| 3. | 8.55 | 16 |
| 4. | 9.4 | 11 |

Effect of Quercetin dihydrate on autocrine growth of HaCat keratinocytes.

Figure 4.

Effect of Allin on autocrine growth of HaCat keratinocytes

Figure5.

Effect of extracts from corn tassels (Tasselin) and tomato paste lycopenes, versus Quercetin on autocrine growth of Ha Cat keratinocytes.

Effect of GTL on Skin Hydration: Vehicle (black bar); GTL (gray bar).

Figure 6.

Effect of AOB on Skin Hydration: Vehicle (while bar); AOB (black bar).

Photograph of volar arm skin of human subject showing A) positive irritant control (0.5% BC only) versus B) 0.5% BC in combination with 5% Tasselin after 24 hours of occlusion.

Chromatograph showing the elution profile of corn tassel (Tasselin) extract versus authentic phenoxyacetic acid methyl ester.

Figure 9A.

UV-spectrum of the corn tassel extract monitored by UV-scan of HPLC fractions.

Figure 10.

Table 3
Antioxidant Activity of Solvent Extracts of Powdered Corn Tassel Pollen Sacs
(DPPH Assay: 75 microliters of sample in duplicate to 3.0 ml of DPPH solution)

| Solvent Extract | O.D. @595nm | Percent Decoloration |
|---|---|---|
| Control DPPH reading | 0.38 | 0 |
| Water (distilled)-1X | 0.045 | 88 |
| Water(distilled)-0.05X | 0.110 | 71 |
| Methanol (absolute)-1X | 0.05 | 87 |
| Ethanol (70% in water)-1X | 0.131 | 66 |

Figure 11

ANTI-IRRITANT BOTANICALS

CROSS-REFERENCE TO RELATED APPLICATIONS

This application claims priority from Provisional Patent Application No. 60/588,460, filed Jul. 16, 2004.

TECHNICAL FIELD OF THE INVENTION

The technical field of the invention is in the area of manufacture of topical ingredients for skin and wound care. More especially in the processing and formulation of ingredients developed from natural products, which possess anti-irritant and/or free radical scavenging antioxidant properties.

BACKGROUND OF THE INVENTION

Among the agents recently proposed for minimizing skin irritation due to skin irritants are fibers (Creton, I., 2002. U.S. Patent Appl., 20020182238A1), and an immune suppressant such as a composition that blocks CD1d activation (Wilson, S. B., 2002. U.S. Patent Appl., 20020165170A1), discloses a method that blocks antigen presentation by skin located immune cells. Lacharriere et al., have proposed the use of a histamine antagonist and or a TNF-alpha antagonist (Lacharriere, O. De; et al., 2001 in U.S. Appl., No.: 20010022978A1).

Historically, plants have been an important source of both new pharmaceuticals and new cosmetic ingredients. Even today plants have yield more new medicinal compounds and cosmetic ingredients than the chemical synthesis approaches exemplified by the recent reliance on combinatorial chemistry methods (C&EN, Oct. 13, 2003).

The search for novel natural products from plants has led to a worldwide search for exotic plants in tropical rainforests of the Amazon and to the ocean depths. This has produced an array of new plant oils that fill the catalogs of commercial cosmetic ingredient suppliers, and to the harvesting of bacteria that inhabit temperature extremes for the purposes of isolating their heat stable enzymes. Yet, it must be noted, that the screening of higher plants for their useful drugs and cosmetic active ingredients has barely scratched the surface of the more than 250,000 species of flowering plants (Angiosperms), and very few of the 50,000 species of monocots (grasses and ornamentals) relatives to the 200,000 species of dicot herbs, shrubs, trees, and ornamentals). Below the flowering plant, aside from a few hallucinogenic mushrooms, and algal plants and bacteria that produce abundance polysaccharide gums, the realm of other plant phyla has been totally neglected. Aside from the lethal phytotoxins from red tides caused by unicellular Dinoflagellates, none of the highly diverse unicellular plants algae have been screened for useful drugs and cosmetics. Thus, it fair to conclude that a systematic and rationale approach to this task has yet to be formulated.

The inventor has taken a different approach to the search for novel botanicals, i.e., plants with medicinal or cosmetic value. This approach narrows the search to plants that grow in the wild, and are cultivated primarily as a foodstuff but for which there is no present commercial medicinal or cosmetic uses. This has led to the discovery of many novel sources of plant derived anti-oxidants some of which are also anti-irritants A truly effective anti-irritant strategy seeks to modulate checkpoints in the irritant signal cascade. Earlier, Wille & Kydonieus (2000) reviewed the scientific and patent literature on anti-irritants. The aim of which was to find new agents useful in prevention and treatment of contact irritant due to topical cosmetic, dermatological and transdermal drugs. In a series of patents (Wille, U.S. Pat. No. 6,670,395, 2003; Wille, U.S. Pat. No. 5,716,987, 1998; Wille and Kydonieus, U.S. Pat. No. 5,843,979, 1998; Wille, Kydonieus and Castellan, U.S. Pat. No. 5,618,557, 1997; Wille and Kydonieus, U.S. Pat. No. 5,686,100, 1997; Wille and Kydonieus, U.S. Pat. No. 5,912,010, 1999; Wille, Kydonieus and Castellana, WO Pat. No. 9,718,782, 1997; Wille and Kydonieus, European Pat. No. 5,612,525, 1994; and in reports (Kalish R, Wood J, Wille J, and Kydonieus A, 1995; Wille, J J., Kydonieus, A., and Kalish, R S., 1998; Wille, J J., Kydonieus, A., and Kalish, R S., 1999a; Wille, J J, Kydonieus, A F., and Murphy, G F., 1999b; Wille, J J., Kydonieus, A F, and Kalish, R S., 2000; Wille and Kydonius, 2001; Wille, Kydonieus and Castellana, WO Pat. No. 9,718,782, 1997), it was shown that ion channel modulators and mast cell degranulating agents were effect anti-irritants and counter-sensitizers. Ethacrynic acid (Edacrinn, Merck) was effective in preventing contact sensitization due to the delivery to mouse skin of four sensitizing drugs: Clonidine, Chlorpheniramine, Albuterol, and Nadolol. Ethacrynic acid, a potassium ion channel blocker, was also effective in preventing skin irritation due to the topical application to mouse of 2,4-dinitro-chlorobenzene, arachidonic acid, phorbol myristic acid, trans-retinoic acid, and lactic acid. The calcium ion channel blockers Nifedipine and Verapamil were effective in minimize contact sensitization in mouse skin due to topical application of the sensitizing and transdermally delivered drug, Nadolol. Phenoxyacetic acid and its alkyl derivatives, non-drug analogs of the diuretic, ethacrynic acid, were shown to prevent contact sensitization due to application to mouse skin of the sensitizing hair dye, para-phenylenediamine and to block skin irritation due a panel of known skin irritants, including anionic surfactants such as sodium lauryl sulfate. Finally, agents which induce mast cell degranulation such as cis-urocanic acid and capsaicin were reported to prevent contact sensitization in a mouse skin model.

Natural products and plant extracts have been the focus of recent interest as emollients and anti-irritants. Castro J (1995) in U.S. Pat. No. 5,393,526 discloses Rosmarinic acid (5%), derived from Sage plant, was able to reduce by more than three-fold the irritating action of alpha-hydroxy acids (lactic and glycolic acids). Pretreatment, one-half hour prior to application of cosmetic formulation containing known skin irritants, by para-aminobenzoic acid and balsam of Peru with extracts the Cola nitida plant, have been disclosed in European Pat. No. Application 0,354,554A2 to prevent skin irritation. Oil from Yerba plants have also been claimed in World Pat. No. Application WO 9,114,441 to eliminate irritation and sensitization that accompanies topical, tranmucosal and transdermal delivery of dihydroergotamine mesylate, acetominophen, oxymetazoline, diphenhydramine, nystatin, clindamycin, and para-aminobenzoic acid. Oils of chamomile, containing chamazulene isolated from yarrow, chamomile and wormwood, were disclosed in U.S. Pat. No. 4,908,213 to be good antipuretics when co-administered in transdermal Nicotine patches.

Depletion of antioxidants is known to cause oxidative damage to human skin (Podda et al, 1998). As discussed above, flavonoids are known to be potent anti-oxidants. Topical replacement of skin anti-oxidants may help to alleviate damage due to ultraviolet radiation and ozone exposure. Flavonoids require stabilization against oxidation by addition of co-reductants such as Vitamin E (α-tocopherol) or Vitamin C (Ascorbic Acid). No mechanism exists to reduce oxidized Vitamin E since there is no Ascorbic acid in the upper layers of the epidermis (stratum corneum). Lazendorfer et al., (2002) in U.S. Pat. No. 6,423,747 discloses cosmetic and dermatological preparations with favonoids having anti-oxidant properties. Illustrative examples mention standard water-in-oil and oil-in-water formations without providing any evidence of their efficacy in these formulations.

Of particular importance to the category of polyphenols and flavonoids is the demonstration (Wille, 2003) that the mechanism of action for many plant-derived anti-irritants is their inhibition of protein tyrosine kinases associated with growth factor receptor stimulated autocrine control of cell proliferation that is the hallmark of many useful skin products that cause skin irritation, i.e., retinoic acid. The use of flavonoids as anti-irritants are among the plant-derived anti-irritants that are readily formulated in the novel hydrophobic delivery system claimed in this patent. They include many plants and herbs are rich in flavonoids as well as flavonoids present in Spanish Honeybee pollen. For example, rutin, quercetin, myricetin, and trans-cinnamic acid; all were present at >350 mg/100 g. Recently, it was reported (Bonina et al, 2002), that Kaempferol is the major flavonoid derived from lyophilized extracts of the flowering buds of capers (*Capparis spinosa* L). This material was shown to have both anti-oxidant and photo-protective effects in human skin.

Antioxidants and free radical scavengers have been employed in many patented formulations for eliminating or minimizing irritation and contact sensitization reactions. Inhivbitors of the metabolites of the arachidonic acid cascade known to be involved in the irritant mechanism of skin have been claimed in European Pat. No. EP 0,314,528A1. Among the designated anti-irritants claimed were Vitamin E, BHT, para-tertiary butyl catechol, hydroquinone, benzoquinone, N,N-diethylhydroxyamine, and nordihydroguaiareic acid.

Vitamin C (ascorbic acid), a water soluble antioxidant, was disclosed in U.S. Pat. No. 5,516,793 to be effective in decreasing skin irritation caused by topical application of such ingredients as: a-hydroxy acids, benzoyl peroxide, retinal, retinoic acid, quaternary ammonium lactates, and salicylic acid. Vitamin E ($\alpha$-tocopherol) is disclosed in U.S. Pat. No. 5,545,407 to reduce skin irritation caused by actives in dermatological preparations containing benzoyl peroxide., and in U.S. Pat. No. 5,252,604 it was disclosed that topical $\alpha$-tocopherol reduced skin irritation due to repeated doses of retinoic acid. Another antioxidant panthenol and its derivatives pantothenic acid, pantethine and pantetheine have been claimed as anti-irritants for formulations containing up to 20% benzoyl peroxide.

The role of antioxidants in protecting the skin from harmful solar exposure, and photoaging is well known. In their book, "Oxidants and Antioxidant in Cutaneous Biology, Thiele and Elsner (2001) have assembled a comprehensive review of free radical chemistry in the skin and the antioxidant network of defense in the stratum corneum. Among the antioxidants discussed for protection of skin are Vitamins E and Vitamin C, green tea polyphenols, resveratol, curcumin, silymarin, ginger, and diallyl sulfide, all of which afford some protection against the development of skin cancer. In addition, the role of carotenoids (lycopenes, luein and $\alpha$, and $\beta$-carotene) as dietary supplements in chemoprevention of cancer were reviewed. The protective effect of topical anti-oxidants against solar radiation result from e.g.: Vitamin E and Vitamin C. Other reported antioxidants that efficiently reduce photodamage include the thiol, N-acetylcysteine and $\alpha$-lipoic acid, which may prevent oxidative stress in skin. In addition, plant-derived flavonoids (apigerneic genistein, catechin, epicatechin, a-glycosylrutin and silymarin) are polyphenols with good antioxidant activity.

Vitamins C and E are routinely used as antioxidants to either stabilize cosmetic ingredients or more recently for their anti-aging free-radical scavenging properties. The most widely used botanical with accepted anti-irritant activity are is Aloe gel; and Witch Hazel (Hammelis Water) containing polymeric proanthocyanidins is by far the best documented case of a botanical anti-irritant. Other botanically-derived actives with potential anti-irritant activity are the catechins and polyphenols, e.g., green tea leaves, and grape seed oil extracts. Additional antioxidants derived from botanicals are Bisabolol, Epigallocatechine, Epigallocatechinegallate Rutin, Quercetin, Hesperidin, Diomine, Mangiferin, Mangostin, Cyanidin chloride, Astaxanthin, Xanthophylls, Lycopene, Reversatrol, Tetrahydrodiferuloylmethane, Rosmarinic acid, Hypericin, Ellagic acid, Chlorogenic acid, Oleoeuropein, Thiotic acid, Glutathione, and Andrographolide (Gupta, 2001). Few of these have been rigorously shown to have anti-irritant activity. Nevertheless, the prospects for broadening the base of plant derived anti-irritants is tremendous because only a small fraction of the over 250,000 known Angiosperm species has been explored.

Here we claim the anti-irritant and antioxidant activity of several new plant-derived anti-irritants. They include a botanical anti-irritant isolated from corn plant tassels, dried lavender flowers, dried flowers of Hops plants, catkins of the Oak tree (*Quercus* sp.), catkins of the Linen tree (*Tialia* sp.), an extract from green tea leaves, green onion leaves; and extract from ripened Autumn Olive berries. These extracts have been incorporated into a novel carrier system (Wille, Novel Delivery Systems, 2004), especially designed to improve their cutaneous delivery.

REFERENCES CITED

U.S. Patent Documents

Creton, I. U.S. Pat. No. Application No.: 20020182238A1. Fibers as anti-irritant agents.

Korneyev, A. Y. U.S. Pat. No. 6,576,269 (Jun. 10, 2003). Treating open skin lesions using extract of sea buckthorn Perricone. U.S. Pat. No. 6,437,004 (Aug. 20, 2002). Treatment of skin damage using olive oil polyphenols.

Wilson, S. B. U.S. Pat. No. Application No.: 20020165170A1. Method of attenuating reactions to skin irritants.

Other Publications:

J J Wille. Provisional Pat. No. Application No.: Novel Topical Delivery System for Plant Derived Anti-irritants (Jul. 4, 2003).

J J. Wille. U.S.P.T.O Disclosure.—"Anti-Irritant Compounds Derived from Plant Extracts (Jun. 18, 2002).

J J Wille. Novel Plant-Derived Anti-Irritants. Abstract in: J. Cosmet. Sci., 54: 106-107, 2003

J J Wille. Novel Topical Delivery System for Plant derived Hydrophobic Anti-Irritant Actives. Abstract presented at National Annual ACS Meeting NY, N.Y. (Sep. 17, 2003).

J J Wille. Plant-derived anti-irritants. In Closing with John Wille. Cosmetics & Toiletries Vol. 118(8): 128, 2003.

J J Wille. Thixogel: Novel Topical Delivery System for Hydrophobic Plant Actives. In: Personal Care Delivery Systems and Formulations Noyes Publication (in press).

J J Wille. Cutaneous delivery of Antioxidant Botanicals. $23^{rd}$ Annual Congress of IFSCC Abstract (October 2004, in press).

SUMMARY OF THE INVENTION

There is disclosed here a method for screening, and then preparing anti-irritant botanical extracts for use in topical formulations in need thereof of a natural ingredient capable of preventing skin irritation when in combination with other active and inactive ingredients that have the potential to irritant skin. In addition, the natural botanical anti-irritants disclosed herein can be topically applied to skin in a formulation without an irritant for the purpose of preventing skin damage due to solar exposure or to oxidant type pollutants in the environment.

Applicant has developed a novel means of screening for potential plant-derived anti-irritants following the strategy and testing assay was developed (USPTO Disclosure Document No. 514152, June 2002). Human epidermal keratinocytes cultured in a serum free culture medium require protein, two growth factors: insulin and epidermal growth factor (EGF) (Wille et al, 1984), by substituting retinyl acetate for EGF one can sustain continued proliferation under autocrine production of HB-EGF (HB-heparin binding), due to retinoid-inducible HB-EGF growth factor receptor (Wille, J. Invest. Dermatol., SID Abstract, 2002). Applicant has shown by use of a specific phosophotyrosine kinase (TRK) inhibitor, that retinoid inducible keratinocyte cell proliferation is dependent on TRK phosphorylation of the insulin growth factor receptor. In light of these discoveries, the inventor postulated that anti-irritants prevent epidermal hyperplasia by blocking retinoid inducible TRK activation of growth factor receptors. Therefore, the search for novel plant-derived anti-irritants involves screening plant extracts that inhibit retinoid-inducible autocrine regulation of human epidermal keratinocyte proliferation in a specially designed clonal growth assay. This assay has uncovered many potential plant-derived anti-irritants.

The methods developed for preparing novel anti-irritant botanicals involves two steps, the sourcing and harvesting of plant materials and a novel processing methods.

The aroma of herbs has been a source of botanicals with health, beauty and medical value since prehistoric times. Minoan archeological (2,500 BC) sites have revealed the use of botanical herbs that are still in use in the present day culinary arts of Crete and Greece (Greek book). As many as 70 different species were recorded by Theophrastus from Crete in Roman times including Dittany, a relative of the herb, Oregano.

The aroma of plants may be used as a to guide to possible sources of new botanicals. In particular, certain phenoxy acids and benzoic acid derivatives have a peculiarly pungent smell. The inventor has previously disclosed that phenoxyacetic acid esters are in fact anti-irritants in U.S. Pat. No. 6,670,395(2003). Thus, the Inventor has relied primarily on his sense of smell to detect and source many novel anti-irritant plants. There include aromatic tassels of corn plants, and the male flowering structures of Oak (*Quercus* genus), Linden (*Tilia* genus) and Mimosa trees. All of which produce hydroalcoholic extracts enriched in anti-oxidants.

Another source of botanicals with potential anti-oxidant and anti-irritant properties are edible plant fruiting bodies; in particular, the ripe red edible berries of Autumn Olive (*Eleagnus umbellate*) trees, and the orange berries of Sea Buckthorn (*Hippophae rhanmoides*), a closely related member of the Eleagnacae family.

Hops (*Humulus lupulus*) grown in Europe since the 14th Century as a bitter substance for brewing of beer was later discovered to contain lupulin, bitter resinous substances (lupulone, humulone) and essential oils in the strobiles from female plants. These lupulins are reputed to have drug like activities for relieving anxiety and inducing sleep. Modern-day cosmetics use this plant in a different form for its beta-hydroxy acids. It is our finding that this scented herb is highly enriched in anti-oxidants.

Green tea leaves are rich in methyl xanthenes (caffeine, theophylline) and antioxidant polyphenols including catchins, and epigallocatechins. They have been the subject of much recent work on topical and dietary use to prevent cancer, and photodamage by exposure to ultraviolet light (UVA and UVB). Hydroalcoholic extracts of dried leaves are disclosed here as a rich source of anti-irritants. Likewise dried powders of cocoa bean plants, or commercial cocoa powder, and green tea leaves, contain both methyl xanthenes and polyphenols. Again, hydroalcoholic extracts of cocoa powder are disclosed here to be a rich source of anti-oxidants. The spice Cinnamon derived from the bark of Cinnamon trees has been reported to contain several polyphenolic compounds an active principle against diabetes (Ag Res Mag., April, 2004), a methyl hydroxychalcone polymer. Hydroalcoholic extracts of pure ground Cinnamon are disclosed here as potent anti-oxidants.

In summary, this patent discloses methods for sourcing new anti-irritant botanicals and identification of anti-irritants among certain male flowering plant parts including corn plant tassels and several the male flowers of deciduous trees. In general, all plant extracts which are rich in anti-oxidants botanicals that also test positive in the in vitro assay for detection of inhibitors of retinoid-stimulated autocrine growth of keratinocytes. These methods have proved to be reliable indicators of anti-irritant activity of plant extracts.

DETAILED DESCRIPTION OF THE INVENTION

EXAMPLE 1

Preparation and Antioxidant Activity of Botanical Extracts

Botanical Extraction:

An equal volume of ice-cold 95% alcohol was added to 100 grams of either dried or wet weight (w/v) of minced plant material and the mixture blended at 23° C. for 2 minutes. The homogenate was clarified by low speed centrifugation at 5° C. and sterile filtered through (0.45 micron filter). All hydroalcoholic extracts so prepared were stored at 0-4° C. and protected from light until further use. Extract concentration was calculated using the percent weight of botanical material to the total volume of botanical weight plus extraction volume. This was 36% (w/v) for Autumn Olive berries (AOB), 5% f (w/v) for Corn Tassel Spikelets (CTS), 11% (w/v) for dried Green Tea Leaves (GTL), 37% (w/v) for Green Onion leaves (GOL), and 36% (w/v) for Red Swiss Chard (RSC, 36% wet weight).

The aromatic corn tassel extract is thus prepared by a method comprising the following steps:
1) harvesting corn tassels at the peak time of their aroma production;
2) blending about equal volumes of alcohol at about 4 degrees C., and minced corn tassel spikelets, to form a 50% hydroalcoholic extract;
3) combining the 50% hydroalcoholic extract with a second extract obtained by re-extracting the once-extracted tassel material with an equal volume of 50% alcohol at about 23 degrees C.;
4) drying the combined hydroalcohlic extracts, followed by several water rinses of airdried powders so formed, followed by dissolving the powder in about 95% alcohol to form a solution; and
5) clarifying the solution, using low speed centrifugation at about 5 degrees C., followed by sterile filtration of the solution.

Anti-oxidant Assay:

Aliquots of botanical hydroalcoholic extracts were assayed for their antioxidant activity by the diphenylpicryl hydrazine (DPPH*) reagent method as described previously (Bonina et al, 2003). In order to standardize the activity of extracts, we defined for each extract an $EC_{50}$ value as the concentration of extract that lowers the zero time optical absorbance of DPPH at 515 nm by 50 percent measured after 30 minutes of incubation at 25° C. Antioxidant activity of extracts was calculated by multiplying its $EC_{50}$ value by a weighting factor representing the percent weight of the starting material in the extract.

Antioxidant Activity of Botanicals.

Figure 1:
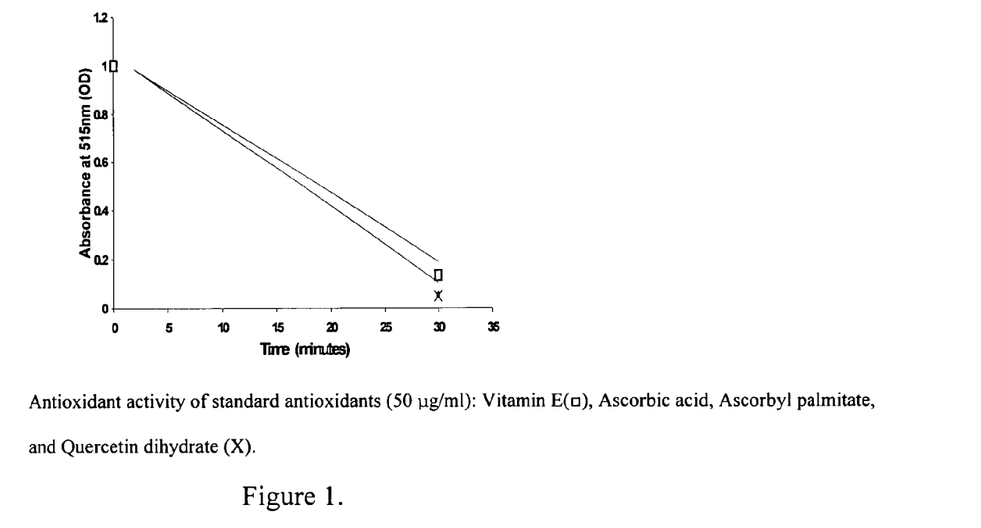
FIG. 1 is a plot of antioxidant activity for standard antioxidants (50 μg/ml): Vitamin E(■), Ascorbic acid, Ascorbyl palmitate, and Quercetin dihydrate (X).

FIG. 1 shows a typical plot of antioxidant activity for several standard antioxidants as assayed by the DPPH* method. The molar activities of ascorbic acid, ascorbyl palmitate and vitamin E were calculated as 26 µM, 30 µM and 46 µM, respectively. Indole acetic acid, a weak free-radical scavenger, had a molar activity of 190 µM, Finally, a commercially purchased flavonoid, quercetin dihydrate; it had an intermediate molar activity of 86 µM.

Figure 2:
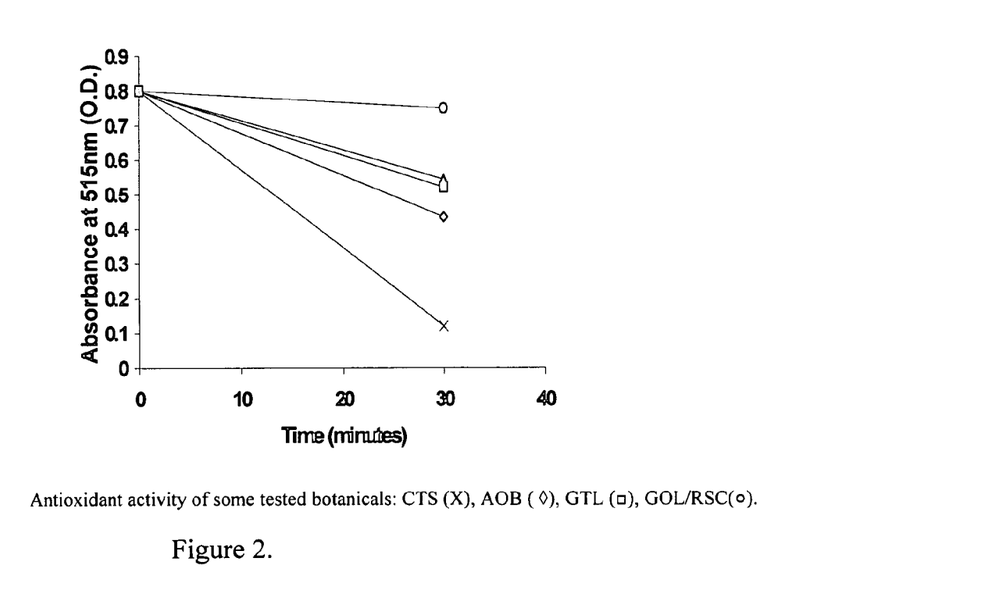
FIG. 2 is a plot of antioxidant activity some tested botanicals: CTS (X), AOB (◇), GTL (■), GOL/RSC(●).
Figure 2A:
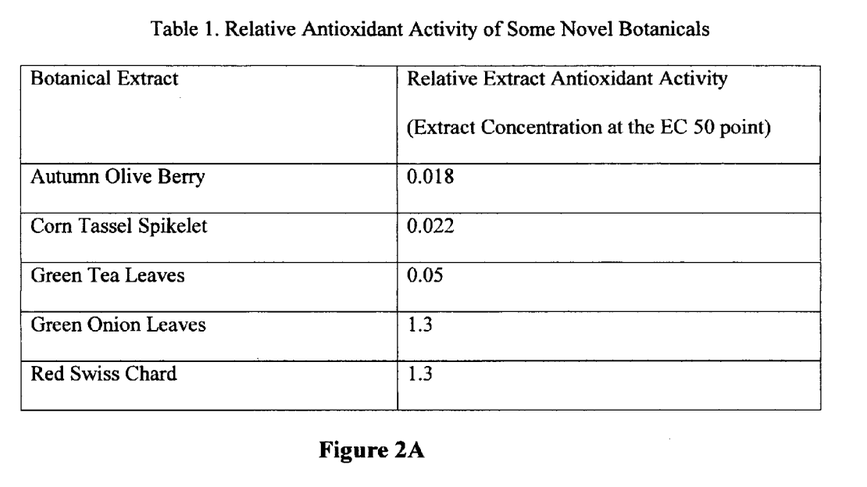
FIG. 2A is a table of the relative antioxidant activity of the botanicals ploted in FIG. 2.

FIG. 2 shows the results of assaying by the DPPH method the antioxidant activity of AOB, GTL, GOL, RSC and CTS. Table 1 (FIG. 2A) presents these results as "Relative $EC_{50}$ Value", i.e., normalized to percent weight of total volume of extract.

We have assayed many other botanical hydroalcoholic extracts for their antioxidant activity including: Aloe leaf, Cocoa powder (Hershey brand), Cinnamon spice, Cranberry (27% juice), grapefruit seed oil (Citricidal®), Hops flowers (*Humulus lupulus*), dried Lavender flowers, ripe red seedless grapes, rhubarb stems, lycopenes purified from tomato paste, carotenes purified carrots, oleic acid, catkins from Linden tree (*Tilia americanus* sp), and catkins from oak tree (*Quercus* sps.), tea tree oil, various commercial food grade vegetable oils, and tomato paste. The majority of these extracts had antioxidant activity less than green tea leaves.

EXAMPLE 2

Use of Retinoid-Stimulated Autocrine (RSA) Growth Assay for Detection of Plant Extracts with Putative Anti-Irritant Activity Since retinoids irritate skin leading to epidermal hyperplasia, it is the inventors idea that plant extracts that act as inhibitors of retinoid -stimulated autocrine growth are themselves anti-irritants. This hypothesis was tested using an in vitro keratinocyte culture model.

An immortalized line of human epidermal kertatinocytes, HaCat keratinocytes, can be cultured in a serum-free culture medium. Sterile Petri dishes (35 mm$^2$) are seeded at 5,000 cells per cm$^2$ and placed in a humidified $CO_2$ incubator at 37° C. for 3-5 days or until the culture reaches about 30% confluent monolayer growth. The dishes are washed once with ice-cold serum-free media lacking EGF and insulin, and refed 2.5 ml of serum-free culture medium containing 5 ug/ml insulin and retinyl acetate (RA, $3\times10^{-8}$ M).—Duplicate control dishes are fixed and stained with 0.2% crystal violet to record the—amount of clonal growth prior to refeeding with fresh RA-containing medium. Test—dishes refed RA and insulin are split into three groups in duplicate. Group A is refed on the RA plus insulin medium. Group B is refed RA plus insulin medium and a TRK inhibitor (PD 15356), and Group C is refed medium containing RA plus insulin and from 0.1 to 5% of a hydroalcoholic botanical extract. All dishes are adjusted to have the same final concentration of alcohol (1%). All dishes are placed back in the incubator for 2 and 4 days. They are fixed and stained with 0.2% crystal violet. The stained dishes are photographed for comparison of results.

Figure 3:
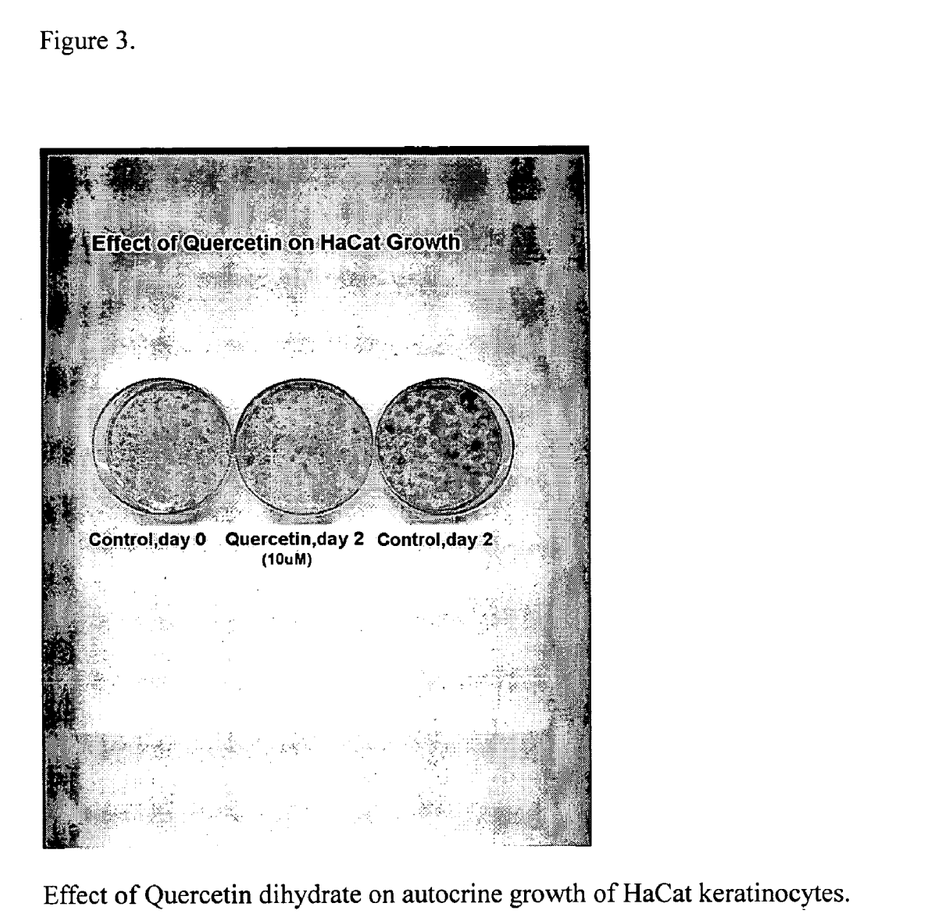
FIG. 3 is a photograph showing the effect of Quercetin dihydrate on autocrine growth of HaCat keratinocytes, cultured under retinoid-stimulated autocrine growth conditions.

As a proof of principle the effect of Quercetin dihydrate (10 µM) a known inhibitor of growth factor receptor TRK on HaCat clonal growth was compared with growth of HaCat cells grown without Quercetin dihydrate, and both cultured under retinoid-stimulated autocrine growth conditions. As predicted, FIG. 3 shows that 48 hours after treatment with Quercetin dihydrate clonal growth was completely inhibited relative to the untreated control.

Figure 4:
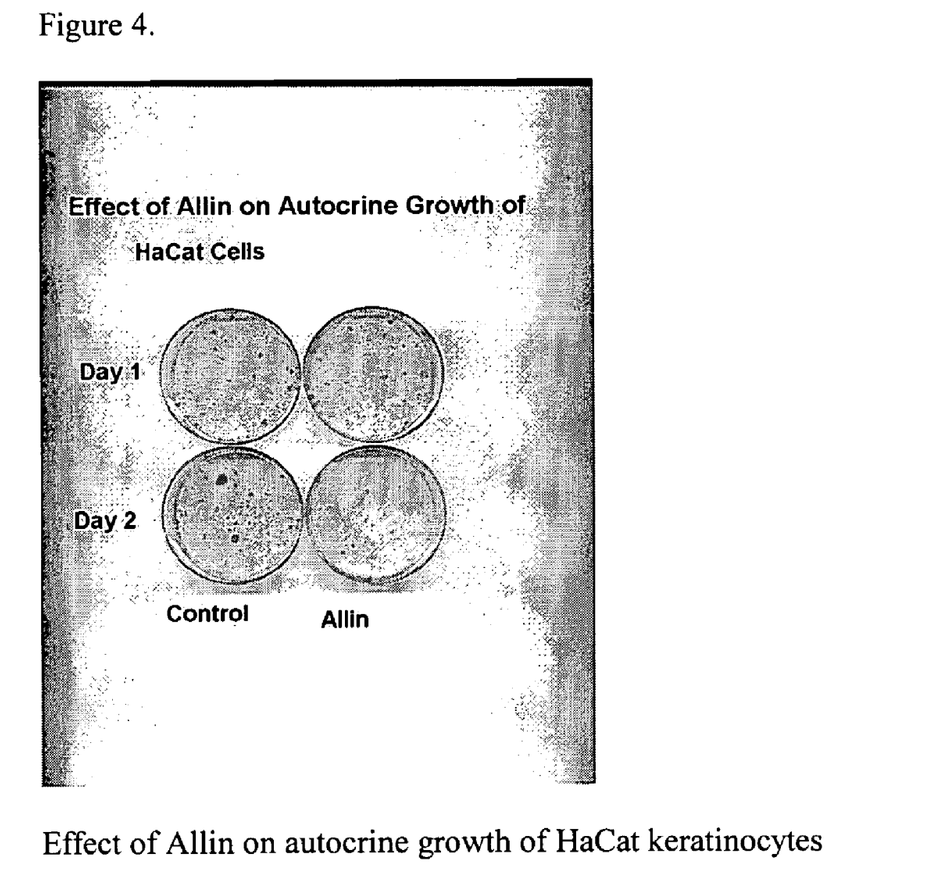
FIG. 4 is a photgraph showing the effect of Allin on autocrine growth of HaCat keratinocytes.

In a second study, the effect of a hydroalcoholic extract of green onion leaves (dubbed Allin) on RSA clonal growth was examined. Green onion leaves have been reported to have 1498 mg/k of the aglycone flavonol Quercetin (Miean et al, 2001). FIG. 4 shows that Allin was effectively inhibited autocrine growth of HaCat keratinocytes.

Figure 5:
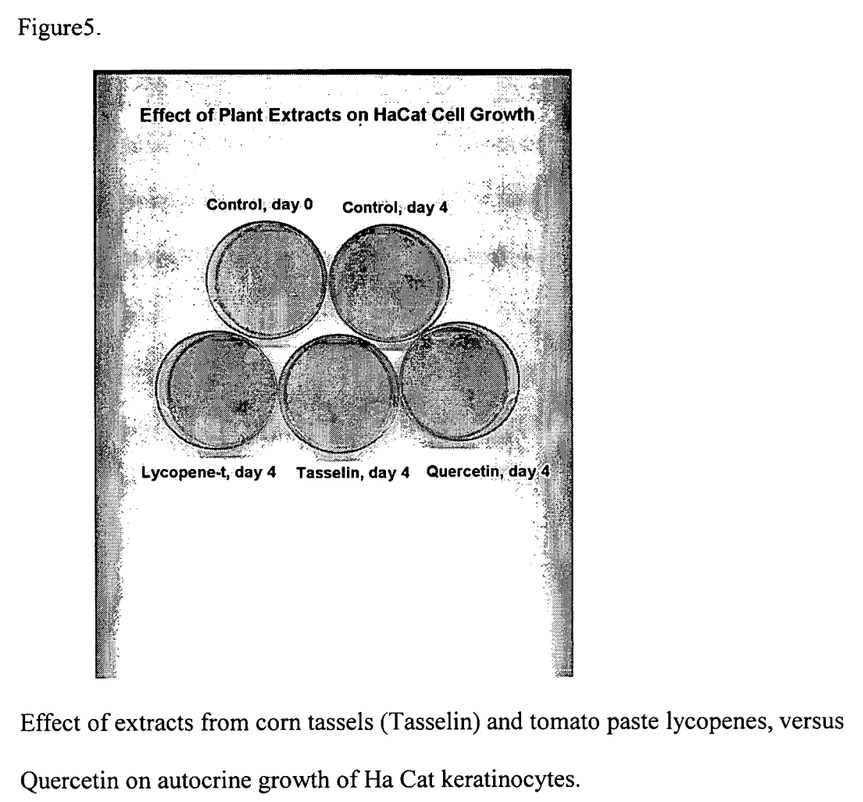
FIG. 5 is a photograph showing the effect of extracts from corn tassels (Tasselin) and tomato paste lycopenes, versus Quercetin on autocrine growth of Ha Cat keratinocytes.

FIG. 5 presents the results of a third study, where the effect of a semi-purified lycopene extract from tomato paste was compared with a hydroalcoholic extract of corn tassels (dubbed Tasselin). A hydroalcoholic solution of Quercetin dihydrate (10 µM) was included as a positive control. The results show that while lycopene had little or no effect, Tasselin was an effective inhibitor of RSA-RTK mediated autocrine regulation of growth of HaCat keratinocytes.

Further studies showed that hydroalcoholic extracts of ripe Autumn Olive berries, extracts prepared from green tea leaves and hydroalcoholic extracts from male flowers (catkins) of Oak and Linden trees were also effective in inhibiting RSA clonal growth of HaCat keratinocytes.

EXAMPLE 3

Anti-irritant Activity of Botanical Extracts

Anti-irritant Assays.

All carrier system gels were prepared with 0.5% benzalkonium chloride, a mild irritant. To test for anti-irritancy, the irritant-containing carrier gels were also loaded with the test botanical extracts (experimentals). The control and test gels were deposited (100 microliters) on 10 mm square circular filter paper discs and placed in side of Finn chambers (20 mm square), which were then applied to the volar arm skin of volunteers. The chambers were affixed to skin with non-allergic adhesive tape and left in place for 24 hours. Upon termination of the treatments, the chambers were removed and the skin gently wiped clean with moistened cotton swabs. The exposed skin was first examined for signs of erythema (redness) and induration (swelling), and skin sites photographed. The exposed skin sites were probed for skin capacitance (skin moisture levels) using a Corneometer instrument (Courage & Khazaka, Koln, Germany).

Figure 6:
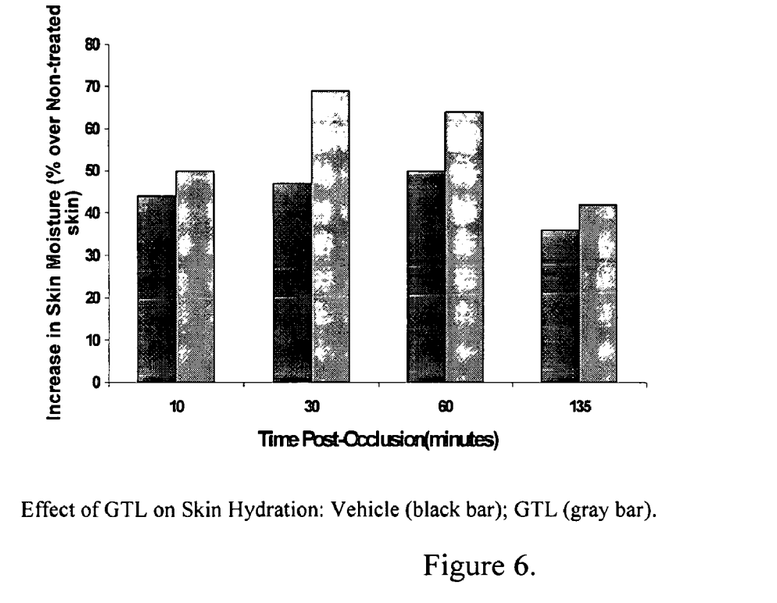
FIG. 6 is a bar chart showing elevated skin hydration following 24-hour occlusion of a 5% GTL extract when co-administered in the carrier gel with a irritating concentration of Benzalkonium Chloride (0.5%). when co-administered in the carrier gel with a irritating concentration of Benzalkonium Chloride (0.5%). Effect of GTL on Skin Hydration: Vehicle (black bar); GTL (gray bar).
Figure 7:
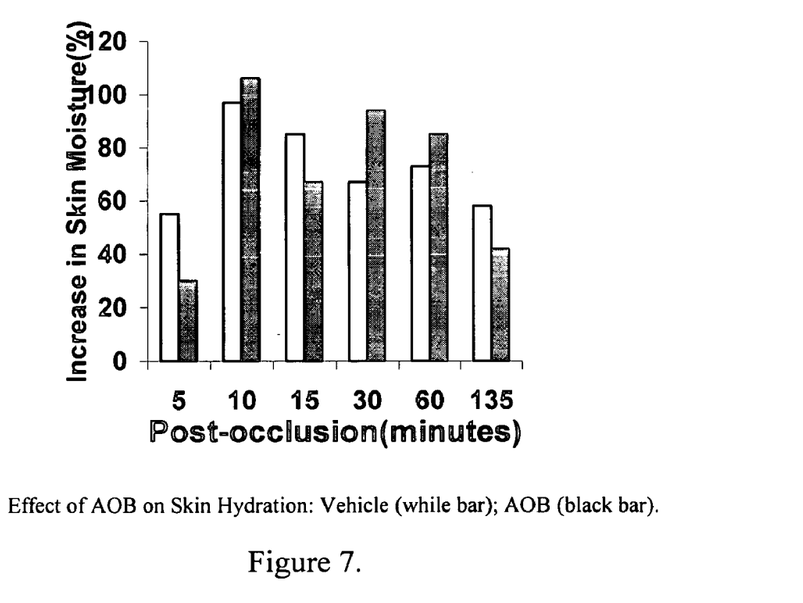
FIG. 7 is a bar chart showing elevated skin hydration effect of AOB on Skin Hydration: Vehicle (while bar); AOB (black bar).

Anti-irritant Activity of Botanicals:

Occlusive patch testing was conducted on extracts prepared by starch gel encapsulation in an oil-in water emulsion system previously described (Wille, 2003). FIG. 6 presents results showing that a 5% GTL extract in vehicle gel elevated skin hydration following 24-hour occlusion when co-administered in the carrier gel with a irritating concentration of Benzalkonium Chloride (0.5%). Similar results were obtained with 5% AOB extract (FIG. 7). The increase in skin hydration may be due to an unexpected moisturizing effect of the botanicals as no visible signs of skin irritation were observed.

Figure 8:
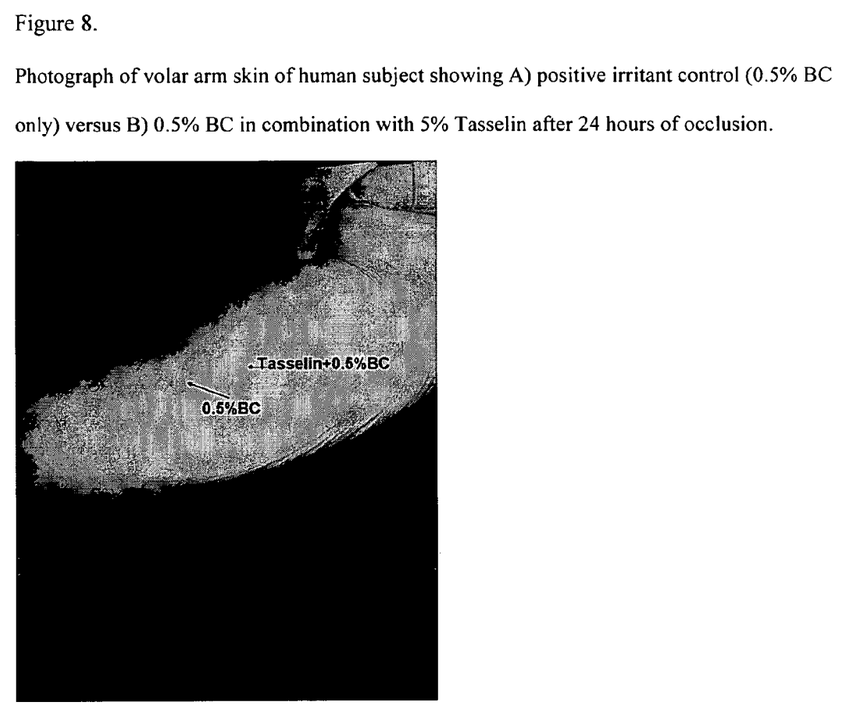
FIG. 8 is a photograph of volar arm skin of human subject showing A) positive irritant control (0.5% BC only) versus B) 0.5% BC in combination with 5% Tasselin after 24 hours of occlusion.

FIG. 8 presents a photograph of volar arm skin exposed for 24 hours under occlusion to vehicle containing 0.5% Benzalkonium chloride (BC), the positive irritation control versus vehicle containing 0.5% BC in combination with 5% Tasselin (corn tassel extract). The photograph shows that Tasselin in the presence of BC suppressed BC-induced redness and skin eruptions seen in the irritant control, i.e., Tasselin is an anti-irritant.

In summary, the results of our studies have demonstrated that the cold-processing and hydroalcoholic extraction methods developed to extract botanicals from dried, powdered or wet weight of plant materials is satisfactory in preserving the anti-oxidant as well as the anti-irritant activity of select botanicals. Among the extracts analyzed, Autumn Olive berries have good antioxidant activities similar to that found for green tea leaf extracts. Although, we have not yet been performed detailed chemical analyses, preliminary work suggests that Autumn Olive berries are rich in polyphenols, while Corn tassel extracts have gallocatechins and polyphenols. The anti-irritant properties of Autumn Olive berry and corn tassel extracts may be due to their antioxidant activity as a oxidative loss of anti-oxidant activity coincides with a loss in anti-irritant activity.

EXAMPLE 4

Partial Chemical Characterization of Corn Tassel Extracts

Figure 9:
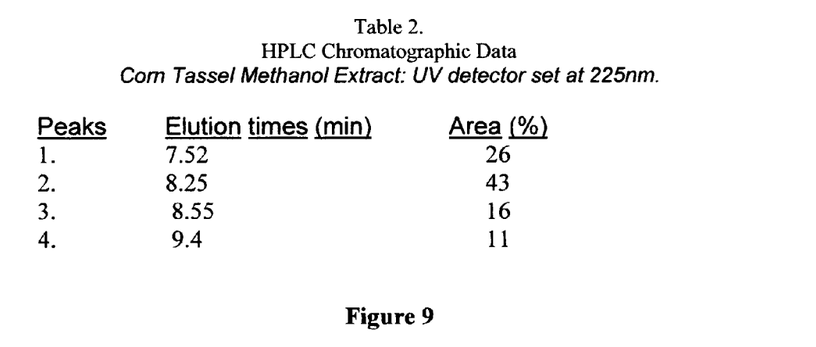
FIG. 9 is a table of Chromatographic data for corn tassel extract in methanol.
Figure 9A:
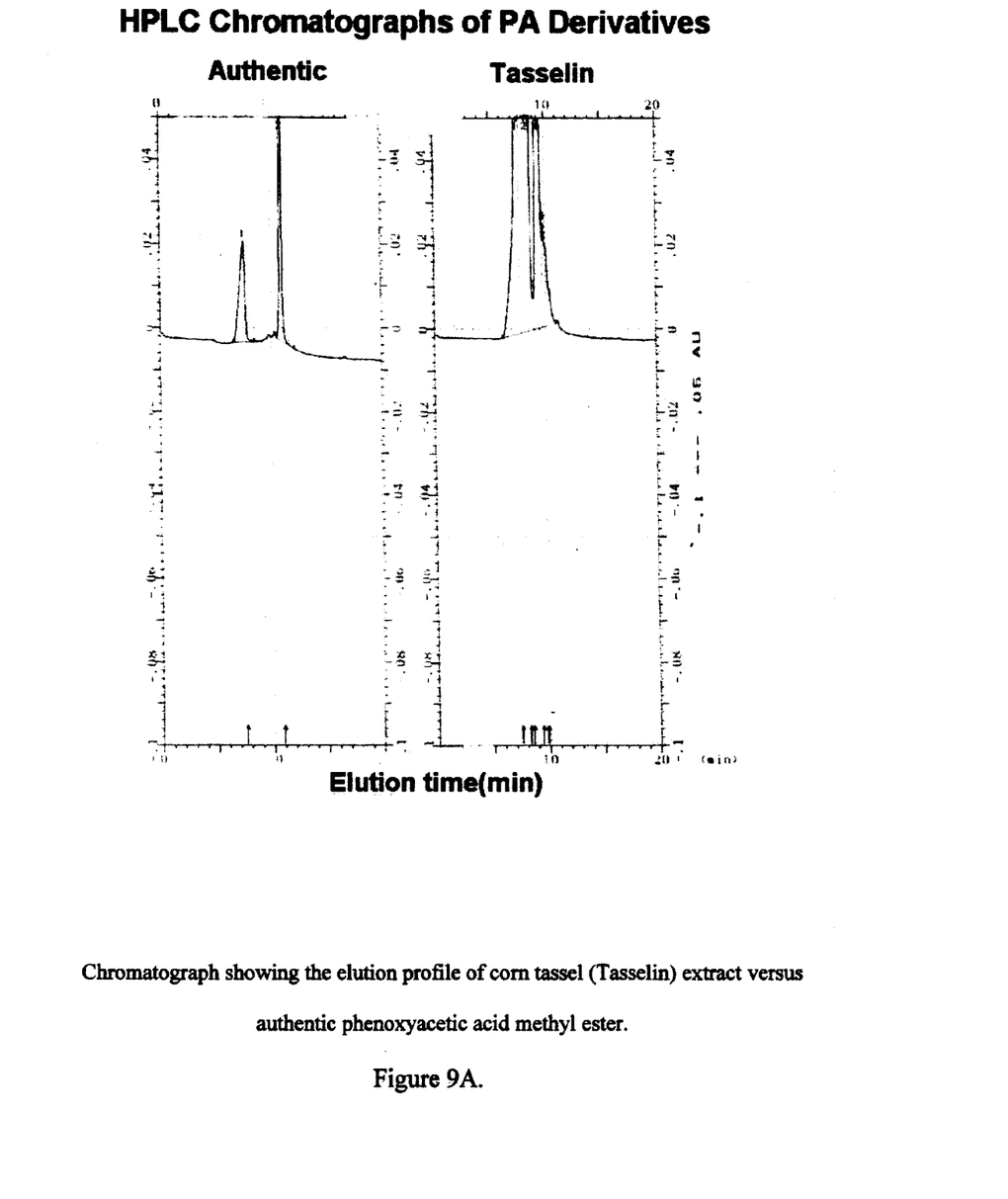
FIG. 9A is a chromatograph showing the elution profile of corn tassel (Tasselin) extract versus authentic phenoxyacetic acid methyl ester.
Figure 10:
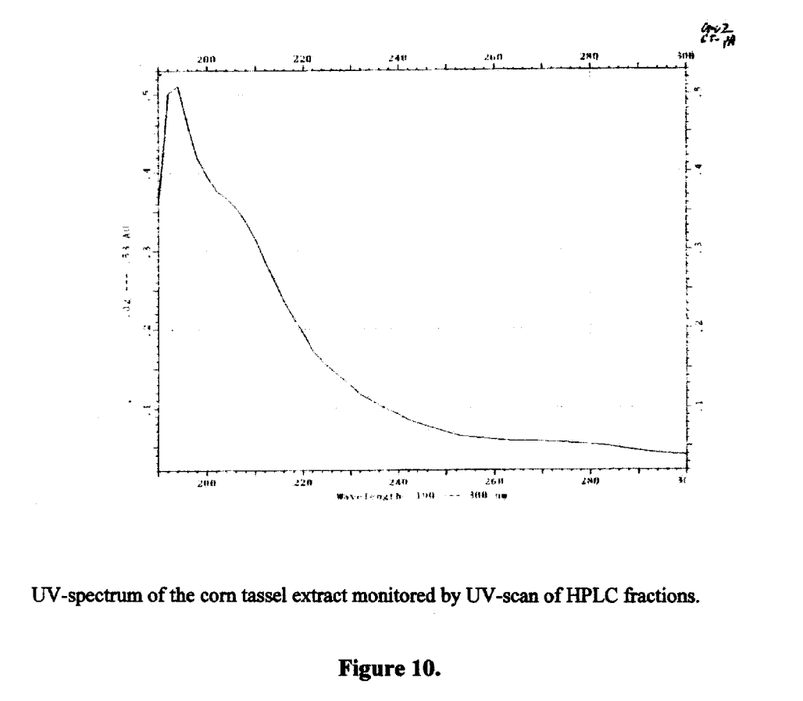
FIG. 10 is a UV-spectragraph of the corn tassel extract monitored by UV-scan of HPLC fractions.

A methanol extract of corn tassels was dried by rotary evaporation and taken up in methanol. The concentrated extract was diluted in chromatographic solvent and used to perform HPLC (high pressure liquid chromatography) studies. Table 2 (FIG. 9) presents the results showing the elution times for the four resolved peaks scanned by the UV-detector at 225 nm. FIG. 9A presents results showing the elution profile of corn tassel (Tasselin) versus authentic phenoxyacetic acid alkyl esters. FIG. 10 shows the UV-spectrum of the corn tassel extract. Note: the peak absorbance is at approximately 190 nm with a secondary peak at about 210 nm.

EXAMPLE 5

Preparation of Anti-oxidant Extracts from Powdered Corn Tassel Spiklets

Figure 11:
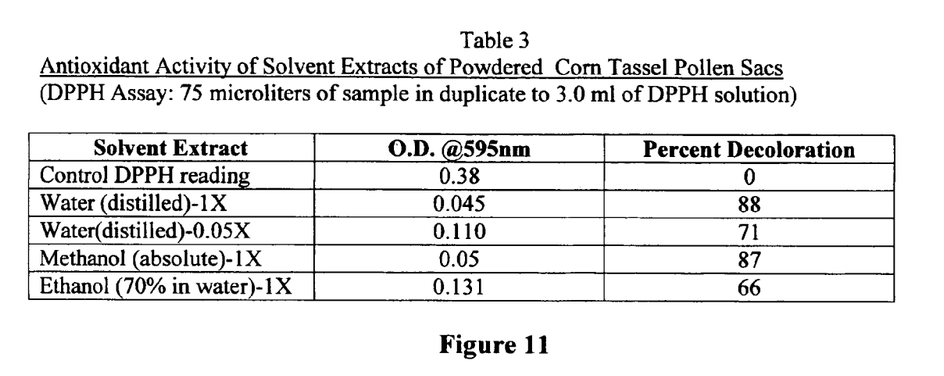
FIG. 11 is a table of antioxidant activity of solvent extracts of corn tassel pollen sacs.

Corn tassel spikelets were collected and stored at −20 degrees centigrade. The material was placed in a clear polyethylene bag and the pollen and spikelet contents shaken loose and recovered separately. The collected pollen and pollen sacs were reddish brown in color and the average particle size was less than 0.5 cm in length. The material so obtained was stored again for varying periods of time at −20 degrees centigrade. For the purposes of the following study, 0.2 grams of dried tassel pollen plus pollen sacs were thawed at room temperature, placed in a ceramic mortar and ground vigorously to a powder with a ceramic pestle. The powdered material was recovered and filtered through a metal cloth mesh (24×24 wires/inch). Greater than 90% of the powdered material passed through the mesh. It was added to a sterile 15 ml conical centrifuge tube and the powdered material was sequentially extracted with 5.0 ml each of a) distilled water, b) 100% methanol and c) 70% ethanol at 25 degrees centigrade. Each final extract was therefore prepared as a 4% (w/v) sample, and were clarified by low speed centrifugation at 5 degrees centigrade for 10 minutes at 3,000 rpm. The resulting solutions were examined for free-radical scavenging activity by the standard diphenyl picryl hydrazine (DPPH*) assay according to the method of Bonina et al (2003). Table (X) presents the results as Percent Decoloration of the DPPH solution after 30 minutes of reaction at room temperature as measured in a Spectrophotometer at 595 nm. The absorbance data are recorded as Optical Density readings.

Note: The water extract had to be diluted 20 fold to obtain a linear reading. The interpolated concentration at which a 50% reduction in color occurred was calculated at a pwder concentration of 0.16%. The Methanol extract of the water-extracted tassel powder material had an equivalent antioxidant activity to the water extract, while the 70% ethanol-water extract had a lower activity, presumably because water and methanol extracts contained the bulk of the antioxidant activity.

The presence of gallo-tannins in the powder extracts was confirmed by development of a positive black color upon drop-wise addition of 10% $FeCl_3$ to a 5% dilution of the 4% (w/v) extracts.

There has thus been shown and described a novel anti-irritant botanical extracts and methods for making the same, of which fulfill all the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

I claim:

1. An aromatic corn tassel extract prepared by the method of:
   1) harvesting corn tassels at the peak time of their aroma production and mincing corn tassel spikelets therefrom;
   2) blending about equal volumes of a 50% aqueous alcohol at about 4 degrees C., and the minced corn tassel spikelets, to form a 50% hydroalcoholic extract;
   3) combining the 50% hydroalcoholic extract with a second extract obtained by re-extracting the once-extracted tassel material with an equal volume of 50% aqueous alcohol at about 23 degrees C.;
   4) drying the combined hydroalcohlic extract to form an air-dried powder followed by dissolving the air-dried powder in about 95% alcohol to form a solution; and
   5) clarifying the solution, using low speed centrifugation at about 5 degrees C., followed by sterile filtration of the solution.

2. A skin care formulation comprising the aromatic corn tassel extract prepared according to claim 1.

3. A method for treating/alleviating skin irritation comprising the step of applying the aromatic corn tassel extract prepared according to claim 1 topically to the skin of a mammal in need thereof.

* * * * *